US006217526B1

(12) United States Patent
Frassica

(10) Patent No.: US 6,217,526 B1
(45) Date of Patent: Apr. 17, 2001

(54) DETACHABLE GUIDEWIRE EXTENSION

(75) Inventor: James J. Frassica, Chelmsford, MA (US)

(73) Assignee: Medtronic AVE, Inc., Santa Rosa, CA (US)

( * ) Notice: Subject to any disclaimer, the term of this patent is extended or adjusted under 35 U.S.C. 154(b) by 0 days.

(21) Appl. No.: 07/681,438

(22) Filed: Apr. 3, 1991

Related U.S. Application Data

(63) Continuation of application No. 07/343,482, filed on Apr. 25, 1989, now abandoned.

(51) Int. Cl.[7] .................................................... A61B 5/00
(52) U.S. Cl. .................................................... 600/585
(58) Field of Search ................................. 128/341, 344, 128/656–8, 14, 772; 604/164, 166, 170, 282; 29/453, 525; 285/304, 318, 330, 345, 382, 382.4; 403/229, 276.7, 297, DIG. 4

(56) References Cited

U.S. PATENT DOCUMENTS

| | | |
|---|---|---|
| 642,193 | 1/1900 | Baeumle . |
| 1,820,644 * | 4/1931 | Bach ................... 385/318 X |
| 2,105,330 | 1/1938 | Pagenkopf . |
| 2,356,835 | 8/1944 | Duckett ..................... 77/55 |
| 2,936,625 | 5/1960 | Heiseler ..................... 74/1 |
| 3,376,060 * | 4/1968 | Tomioka ................. 285/382 |
| 3,440,334 | 4/1969 | Blomstrand ............... 174/87 |
| 3,515,027 | 6/1970 | Textrom ..................... 85/32 |
| 3,517,184 | 6/1970 | Norton et al. ............. 240/7.5 |
| 3,888,598 | 6/1975 | Samiran et al. .......... 403/372 |
| 4,732,163 * | 3/1988 | Bonello et al. ........... 128/772 |
| 4,785,489 * | 11/1988 | Von Doehren ......... 403/229 X |
| 4,827,941 * | 5/1989 | Taylor et al. ......... 128/772 X |
| 4,875,489 * | 10/1989 | Messner et al. ........... 128/772 |

FOREIGN PATENT DOCUMENTS

2180454 * 4/1987 (GB) .................... 128/772

* cited by examiner

*Primary Examiner*—Max Hindenburg
(74) *Attorney, Agent, or Firm*—Sterne, Kessler, Goldstein & Fox PLLC

(57) ABSTRACT

A guidewire system for use in catheter exchanges avoids the need for a separate exchange wire by connecting an extension wire to the proximal end of the guidewire thereby increasing the effective length of the guidewire to permit a catheter exchange. The proximal end of the guidewire is attached to the distal end of the exchange wire by a disconnectable, reattachable connection which avoids deformation of the connected joint. The connection includes a male element in the form of a reduced diameter rod extending axially from the proximal end of the guidewire and a female element attached to the distal end of the extension wire. The female element includes a helical coil receptive to the rod and dimensioned to receive the rod in an interference fit requiring the spring to expand. Separation is effected by imparting a combined twisting and axial separation motion to the guidewire and extension wire.

7 Claims, 1 Drawing Sheet

DETACHABLE GUIDEWIRE EXTENSION

This application is a continuation of application Ser. No. 07/343,482, filed Apr. 25, 1989, now abandoned.

FIELD OF THE INVENTION

This invention relates to guidewires used in guiding of catheters and to devices and techniques for extending the effective length of the guidewires to facilitate catheter exchanges.

BACKGROUND OF THE INVENTION

In some catheterization techniques, it is desirable to use a series of catheters in order to complete effectively the procedure at hand. For example, in percutaneous transluminal coronary angioplasty procedures in which a balloon catheter is advanced into a stenosed region of the patient's coronary artery and is inflated within the stenosis to dilate the lumen of the artery, it is not uncommon for the physician to require the sequential use of several balloon dilatation catheters having balloons of progressively increasing size. Typically, such catheters are used in connection with a guidewire that extends through the catheter and serves as a guide over which the catheter may be advanced to the stenosis. When performing such a catheter exchange, it is important to do so without shifting and losing the position of the guidewire in the entry so that the guidewire may be used to guide the next catheter to the stenosis. In order to maintain guidewire position, conventional practice has been to use a relatively long exchange wire. The exchange wire, which typically is of the order of 300 cm long (as compared to a conventional guidewire length of the order of 175 cm) is first exchanged for the conventional guidewire by removing the conventional guidewire from the existing catheter and replacing it with the longer exchange wire. Then the existing catheter is withdrawn over the exchange wire, the exchange wire being sufficiently long so that it is never completely covered by the withdrawn catheter thereby enabling the exchange wire to be held in position by the physician or an assistant during the catheter withdrawal. After the initial catheter is removed, the succeeding catheter is advanced over the exchange wire which guides the second catheter to the stenosis. The exchange wire then may be removed and may be replaced with a conventional guidewire which, typically, will be more easily manipulated during the angioplasty procedure.

The foregoing procedures are time consuming and somewhat awkward. A significant advance in the technique for effecting catheter exchanges has been developed and has been in use which involves a system that enables exchange of catheters without using exchange wires. In brief, that system utilizes an extension wire that is attached to the proximal end of the guidewire already in place in the patient. That effectively extends the overall length of the guidewire to that needed for the catheter exchange. The system uses a connection in which the distal end of an extension wire is telescoped together with the proximal end of the guidewire and the junction then is crimped, thus, retaining the wires together by deforming them at their juncture. The crimp is intended to present low resistance to the catheter as it is passed over the connection. Some resistance, however, does result and it has not before been possible to completely eliminate the resistance presented by the crimp. Further inconvenience with the crimped system is that it requires the use of a separate crimping tool. When the guidewire and extension wire are detached, they cannot be reconnected or reused easily because of the deformation formed during their connection. Thus, some inconvenience is presented should it be desirable to make multiple catheter exchanges.

It is among the general objects of the invention to provide an improved connection system for a guidewire and an extension wire.

SUMMARY OF THE INVENTION

In accordance with the present invention, a connection system for a guidewire and guidewire extension utilizes a telescoping connector that is self-latching, disconnectable and reconnectable without deformation of the guidewire or the extension. The connection enables the guidewire extension to be attached for a catheter exchange, then disconnected after the catheter exchange is complete to permit the guidewire and catheter to be manipulated and operated conventionally. Should another catheter exchange be required, the extension wire, which may be reused, is simply reconnected to the proximal end of the guidewire and the catheter exchange procedure may be repeated. The number of guidewire-extension wire connections and disconnections are unlimited as is the number of catheter exchanges that may be performed with the system.

More particularly, the guidewire is provided with a reduced diameter rod that is adapted to mate with a connector socket on the distal end of the extension wire. The extension wire includes a shaft having, on its distal end, a socket adapted to receive and become securely attached to the rod on the proximal end of the guidewire. The connector mounted on the distal end of the wire extension includes a tubular housing attached to the distal end of the extension wire. The tubular housing has an opening at its distal end which receives the wire on the proximal end of the guidewire. A helical coil is contained within the housing and is attached at its proximal end to the proximal end of the housing and distal end of the wire extension shaft. The coil has an outer diameter slightly less than the inner diameter of the housing. The opening at the distal end of the housing is defined by a surrounding inwardly extending lip which is dimensioned to present an obstruction to distal extension of the helical coil within the housing. The inner diameter of the coil is less than the outer diameter of the rod extending from the proximal end of the guidewire. The guidewire and extension wire may be connected simply by inserting the rod at the proximal end of the guidewire into the opening at the end of the housing on the wire extension. The rod is urged into the housing and into the helical coil which causes the helical coil to expand to receive the slightly larger diameter rod. It may be necessary to impart a slight rotation to the wire extension in order to facilitate the extension. Once connected, the attachment is secure and will withstand substantial separation forces without disconnecting. The wire extension and guidewire may be detached simply by rotating the extension wire with respect to the guidewire and while doing so, axially separating the two. The rotation of the helical coil with respect to the rod relaxes the grip of the coil on the rod, thus permitting the two to be separated under a light separation force.

It is among the general objects of the invention to provide an improved guidewire extension system.

A further object of the invention is to provide an improved guidewire extension system which is self-latching and does not require deformation of the joint between the guidewire and guidewire extension.

Another object of the invention is to provide a connection system for a guidewire and guidewire extension which is disconnectable and reconnectable.

Another object of the invention is to provide a guidewire and extension and connection system therefor which minimizes impedance to advancement of a catheter over the joint.

DESCRIPTION OF THE DRAWINGS

The foregoing and other objects and advantages of the invention will be appreciated more fully from the following further description thereof, with reference to the accompanying drawings wherein.

DESCRIPTION OF THE PREFERRED EMBODIMENT

Figure 1:
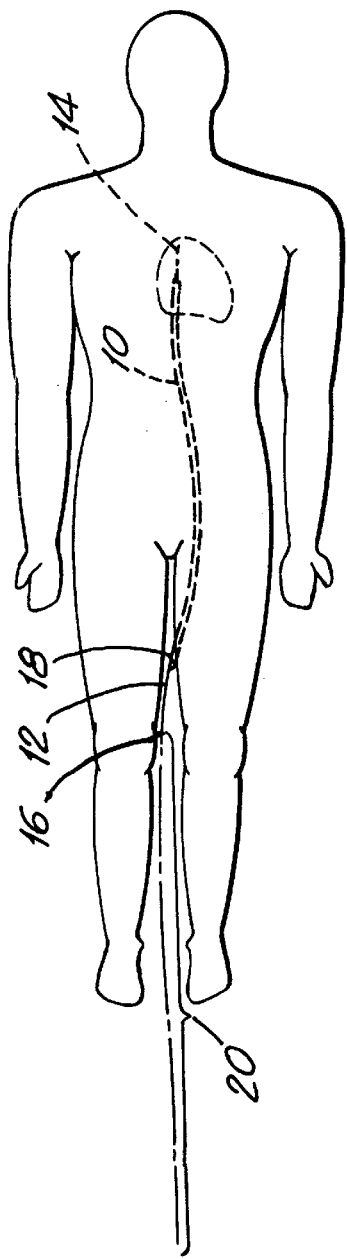
FIG. 1 is a diagrammatic illustration of a patient undergoing catheterization showing the guidewire and, in phantom, the exchange wire.

FIG. 1 illustrates, in highly diagrammatic form, the catheter 10 and guidewire 12 which have been inserted into a patient's femoral artery and have been advanced through the region of the patient's heart where the desired procedure will be performed. The guidewire 12 and catheter 10 will have been inserted and placed in the artery in accordance with well known procedures. When it is desired to perform a catheter exchange, the conventional practice has been to remove the guidewire 12 from the catheter 10 and replace it with a long exchange wire. Then the catheter 10 could be removed over the exchange wire and the next catheter could be introduced into the patient over the exchange wire. Then the exchange wire would be removed and replaced with a shorter, conventional guidewire.

In accordance with the present invention, catheters may be exchanged without requiring removal of the guidewire 12 and without requiring the involvement attended to the use of an exchange wire. In the practice of the present invention, the guidewire 12 is connected at its proximal end to an extension wire 20 while the guidewire 12 and catheter 10 remain in the patient. The extension wire 20 is attached securely to the proximal end of the guidewire 12 and serves to extend the effective length of the guidewire 12 sufficiently to permit the catheter 10 to be withdrawn over the guidewire 12 and extension 20. Moreover, the present invention utilizes an improved connection between the guidewire and extension wire.

Figure 2:
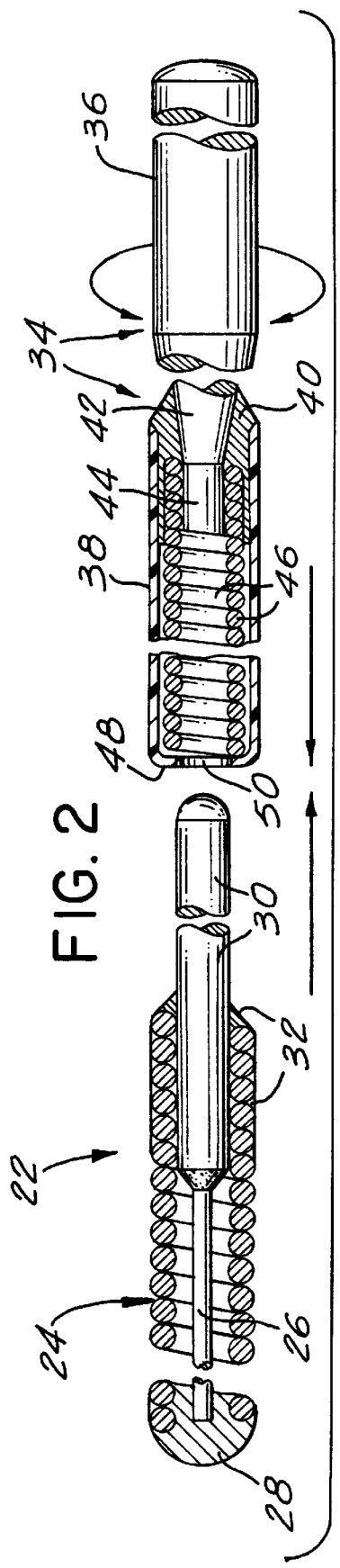
FIG. 2 is a fragmented illustration of the guidewire and extension wire in accordance with the invention.

FIG. 2 shows a guidewire 22 modified in accordance with the present invention. The guidewire 22 may be of the type having a helical coil 24 extending fully along its length from its proximal to its distal end. A safety wire or core wire 26 is secured to the proximal end of the coil 24 and also at the distal end of the guidewire, such as by connection to a hemispherical tip weld 28 at the distal end of the coil 24. By way of example, the guidewire may be of the order of 175 cm long and may have an outer diameter of about 0.018". Attached to and extending proximally from the proximal end of the helical coil 24 is an axially extending rod having an outer diameter of between about 0.009" to about 0.013". The rod is received within the proximal end of the coil and is secured thereto as by brazing 32. The distal end of the rod is contained within the helical coil 24 and is attached, as by brazing, to the proximal end of the safety wire 26. By way of example, the rod 30 may extend from the proximal end of the coil 24 about ½".

FIG. 2 also shows the extension wire 34 which may be in the form of a solid elongate shaft 36. A tubular housing 38 is attached to the distal end of the shaft 36 as by a brazed joint 40. The distal end of the shaft 36 is tapered as at 42 and may terminate in a short cylindrical tip 44 that is received in the proximal end of a helical coil 46. The helical coil 46, distal tip of the shaft 44 and the housing 38 all are secured together at the brazed joint 40. The helical coil may be formed from wire 0.002" in diameter. The coil may be approximately 0.5" in length. The coil may have an internal diameter of 0.007" and an outer diameter of 0.11". The housing 38 has an internal diameter several thousandths of an inch greater than the outer diameter of the coil 46. The housing is slightly longer than the coil and may be of the order of 0.625" long. The distal end of the housing 38 is formed to include an inwardly turned annular lip 48 that defines an opening 50 in the distal end of the housing. The diameter of the opening 50 is between the inner and outer diameter of the coil 46 to permit the coil from becoming stretched and elongated under the influence of an axial separation force when the guidewire 22 and guidewire extension 34 are connected.

The guidewire 22 and guidewire extension 34 are connected simply by inserting the rod 30 into the housing 38 and into the coil 46. Some twisting of the extension wire 34 may facilitate the connection although, depending on the relative diameter of the rod 30 and the inner diameter of the coil 46, the two may be connected simply by axial motion without relative rotation. The several thousandths of an inch clearance between the outer diameter of the coil 46 and the inner diameter of the housing 38 permits the coil 46 to expand slightly as the slightly larger diameter rod 30 is inserted into the inner diameter of the spring 46. The grip effected between the helical coil 46 and the rod 30 is quite strong and will withstand several pounds of axial separation force. The coil 46, however, will not become elongated under the influence of such an axial separation force because the lip 48 at the distal end of the housing serves to contain the distal end of the spring 46 and prevents it from expanding lengthwise. When it is desired to detach the guidewire 22 and extension wire 34, a simple rotation of the extension wire 34 with respect to the rod loosens the connection between the coil 46 and rod 30 and, while so twisting they may be separated by also imparting an axial separation force.

The guidewire 22 and extension wire 34 may be reconnected and disconnected as many times as desired, thus permitting repeated use of the extension wire. The outer diameter of the extension wire shaft 36 and housing 38 as well as the outer diameter of the coil 24 of the guidewire are substantially the same so that the connection made is smooth and continuous and does not provide any impedance to movement of the catheter over the joint.

Figure 3:
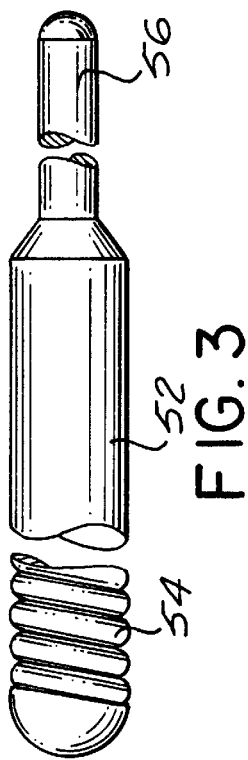
FIG. 3 is a fragmented illustration of the invention with a different type of guidewire.

FIG. 3 illustrates the invention used with another type of guidewire in which the proximal end of the guidewire is formed from a solid shaft. For example, such a guidewire may be of the type disclosed in U.S. Pat. No. 4,545,390 (Leary). The Leary type of guidewire has an elongate stainless steel shaft 52 having a proximal end formed from a solid or tubular wire and a distal end that carries a helical coil 54. With this type of guidewire, a rod 56 is formed at its proximal end by grinding down the proximal end of the shaft 52 to define the pin. Should shaft 52 of this type of guidewire be hollow, a rod may be inserted into the lumen of the tube at its proximal end and may be brazed in place. The operation and function of such guidewires with the connector disclosed in FIG. 2 is the same as described above.

From the foregoing, it will be appreciated that the invention provides an improved connection system for a guidewire and a guidewire extension that does not require the use of crimped joints or other means to deform permanently the guidewire and extension. The invention enables the extension to be connected, detached and then reconnected which permits multiple catheter exchanges should that be desired. Moreover, the joint provides a smooth uncrimped connection over which the catheters may be advanced easily and with minimal resistance.

It should be understood, however, that the foregoing description of the invention is intended merely to be illustrative thereof and that other modifications and embodiments may be apparent to those skilled in the art without departing from the spirit.

Having thus described the invention, what I desire to claim and secure by Letters Patent is:

1. A guidewire for use with a catheter and an extension for the guidewire for enabling multiple catheter exchanges comprising:

a guidewire having a proximal end and a distal end;

an extension wire having a proximal end and a distal end;

the proximal end of the guidewire having a rod extending proximally and axially therefrom, the rod being of a diameter smaller than that of the guidewire;

a connector carried by the distal end of the extension wire, the connector being adapted to receive the rod on the proximal end of the guidewire to become securely attached to the rod while permitting the rod and connector to be detached, the connector comprising a helical coil having proximal and distal ends, the proximal end of the helical coil being attached to the distal end of the extension wire, the distal end of the coil being open;

means for precluding substantial axial extension of the helical coil;

the inner diameter of the helical coil being slightly less than the outer diameter of the rod on the guidewire;

whereby the rod may be inserted into the open end of the helical coil, the helical coil expanding to receive the rod and securely gripping the rod.

2. A guidewire and extension therefor as defined in claim 1 further comprising:

means defining an annular ring-like element disposed distally of the open end of the coil, the ring-like element having an inner diameter smaller than the outer diameter of the coil;

means for retaining the ring-like element in said position so as to preclude extension of the helical coil beyond said ring-like annular element.

3. A guidewire and extension therefor as defined in claim 2 further comprising;

a tubular housing mounted to the distal end of the extension wire and extending distally therefrom, the housing containing the helical coil;

said annular distal ring-like element comprising an inwardly turned annular lip formed at the distal end of the housing;

the internal diameter of the housing being several thousandths of an inch greater than the outer diameter of the helical coil when the helical coil is relaxed, said internal diameter of the housing being greater than the outer diameter of the helical coil when the rod is inserted in the open end of the helical coil.

4. A guidewire and extension therefor as defined in any of claims 1–3 wherein the guidewire and extension wire are detachable by effecting a relative twisting motion between the wire extension and the guidewire, thereby to relax the grip of the helical coil on the rod and simultaneously imparting an axial separation motion to the guidewire and extension wire.

5. A guidewire and extension wire therefor as defined in claim 1 wherein the guidewire and extension wire are detachable by effecting a relative twisting motion between the wire extension and the guidewire, thereby to relax the grip of the helical coil on the rod and simultaneously imparting an axial separation motion to the guidewire and extension wire.

6. A guidewire extension system comprising:

an extension wire adapted to be releasably but firmly connected to a proximal end of a guidewire, said extension wire having a distal end and a proximal end, and a connecting assembly mounted at the distal end of said extension wire and including a helical coil constructed and arranged to receive and grippingly engage and lock against a proximal end of the guidewire; and a small diameter tubular housing received over said helical coil and fixed to said distal end of said extension wire, said tubular housing having maintaining means within the distal end portion of said tubular housing for maintaining said helical coil in said tubular housing.

7. A guidewire extension system comprising:

an extension wire adapted to be resiliently but firmly connected to a proximal end of a guidewire, said extension wire having a distal end and a proximal end, and a connecting assembly mounted at the distal end of said extension wire and including a helical coil constructed and arranged to receive and grippingly engage and lock against a proximal end of the guidewire; and a small diameter tubular housing received over said helical coil and fixed to said distal end of said extension wire, said tubular housing having a radially inwardly, extending projection within the distal end portion of said tubular housing and engageable with the helical coil to prevent the helical coil from extending out of said tubular housing.

* * * * *